United States Patent
Sharma et al.

(10) Patent No.: US 10,196,397 B2
(45) Date of Patent: Feb. 5, 2019

(54) PROCESS FOR THE PREPARATION OF IBRUTINIB

(71) Applicant: Sun Pharmaceutical Industries Limited, Mumbai, Maharashtra (IN)

(72) Inventors: Kapil Sharma, Amritsar (IN); Bhavin Prabhudas Thanki, Junagadh (IN); Mahavir Singh Khanna, New Delhi (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/528,228

(22) PCT Filed: Nov. 18, 2015

(86) PCT No.: PCT/IB2015/058933
§ 371 (c)(1),
(2) Date: May 19, 2017

(87) PCT Pub. No.: WO2016/079693
PCT Pub. Date: May 26, 2016

(65) Prior Publication Data
US 2017/0320879 A1    Nov. 9, 2017

(30) Foreign Application Priority Data

Nov. 19, 2014 (IN) .......................... 3343/DEL/2014

(51) Int. Cl.
*C07D 487/04* (2006.01)
(52) U.S. Cl.
CPC ................ *C07D 487/04* (2013.01)
(58) Field of Classification Search
CPC ........................ A61K 31/519; C07D 487/04
USPC ...................... 514/262.1; 544/262
See application file for complete search history.

(56) References Cited

U.S. PATENT DOCUMENTS

| 6,921,763 | B2 | 7/2005 | Hirst et al. ................. 514/258 |
| 8,158,786 | B2 | 4/2012 | Honigberg et al. ........... 544/262 |
| 8,673,925 | B1 | 3/2014 | Goldstein .................. 514/262.1 |
| 9,533,991 | B2* | 1/2017 | Chen .................. A61K 31/4162 |
| 2002/0156081 | A1 | 10/2002 | Hirst et al. .................... 514/247 |
| 2007/0293516 | A1 | 12/2007 | Knight et al. ............ 514/262.1 |
| 2014/0221333 | A1 | 8/2014 | De Man et al. ......... 514/210.02 |

FOREIGN PATENT DOCUMENTS

| CN | 103121999 | 5/2013 | ........... C07D 487/04 |
| CN | 103626774 | 3/2014 | ........... C07D 487/04 |
| WO | WO 02/076986 | 10/2002 | ........... C07D 487/04 |
| WO | WO 2007/126841 | 11/2007 | ............ A61K 31/33 |
| WO | WO 2010/006086 | 1/2010 | ........... C07D 487/04 |
| WO | WO 2011/094628 | 8/2011 | ........... C07D 487/04 |
| WO | WO 2012/003544 | 1/2012 | ........... C07D 487/04 |
| WO | WO 2013191965 A1 | 12/2013 | |

OTHER PUBLICATIONS

Ho et al., "Efficient Synthesis of $^{14}$C-Labeled 1H-Pyrazolo[3,4-d]pyrimidine and Related [4.3.0]-Bicyclic Pyrimidino Systems," *Helvetica Chimica Acta*, 91(5):958-963 (2008).
Co-pending PCT Application No. PCT/IB2015/058933, filed Nov. 18, 2015, published as WO 2016/079693 on May 26, 2016.
International Search Report and Written Opinion for International Application No. PCT/IB2015/058933, issued by US/ISA dated Feb. 9, 2016.
International Preliminary Report on Patentability for International Application No. PCT/IB2015/058933, issued by WIPO dated Jun. 1, 2017.
EPO Extended Search Report dated Mar. 23, 2018 for EPO Application No. 15860646.7.

* cited by examiner

*Primary Examiner* — Jeffrey H Murray

(57) ABSTRACT

The present invention provides processes for the preparation of ibrutinib, intermediate compounds of Formula VI and Formula VIII, and salts thereof. The processes of the present invention are commercially viable, cost-effective, environmentally friendly, and make use of inexpensive, non-hazardous, safe chemicals that are easy to handle.

12 Claims, No Drawings

PROCESS FOR THE PREPARATION OF IBRUTINIB

FIELD OF THE INVENTION

The present invention provides processes for the preparation of ibrutinib, intermediate compounds of Formula VI and Formula VIII, and salts thereof.

BACKGROUND OF THE INVENTION

Ibrutinib is 1-[(3R)-3-[4-amino-3-(4-phenoxyphenyl)-1H-pyrazolo[3,4-d]pyrimidin-1-yl]-1-piperidinyl]-2-propen-1-one, represented by Formula I.

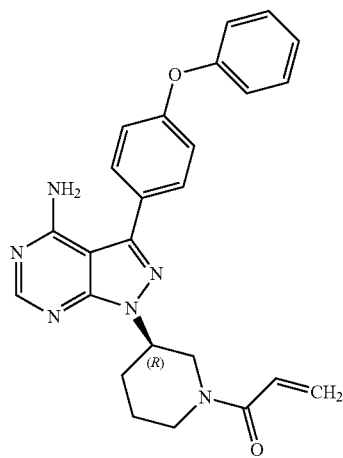

Formula I

Ibrutinib is an inhibitor of Bruton's tyrosine kinase (BTK).

U.S. Pat. No. 8,158,786 describes a process for the preparation of ibrutinib.

Chinese Publication Nos. CN 103121999 and CN 103626774 also describe processes for the preparation of ibrutinib.

SUMMARY OF THE INVENTION

The present invention provides processes for the preparation of ibrutinib, intermediate compounds of Formula VI and Formula VIII, and salts thereof. The processes of the present invention are commercially viable, cost-effective, environmentally friendly, and make use of inexpensive, non-hazardous, safe chemicals that are easy to handle.

DETAILED DESCRIPTION OF THE INVENTION

The term "about," as used herein, refers to any value which lies within the range defined by a number up to ±10% of the value.

The term "room temperature," as used herein, refers to the temperature in the range of about 25° C. to 35° C.

The term "halogen," as used herein, refers to chloro, bromo, or iodo.

The term "lower alkyl," as used herein, includes both straight chain and branched chain alkyl groups having 1 to 6 carbon atoms, for example, methyl, ethyl, propyl, iso-propyl, n-butyl, sec-butyl, iso-butyl, tert-butyl, n-pentyl, iso-pentyl, n-hexyl, and iso-hexyl.

The term "salt," as used herein, refers to a salt prepared from an inorganic or an organic acid. Examples of inorganic acids include hydrochloric acid, hydrobromic acid, hydroiodic acid, sulfuric acid, nitric acid, and phosphoric acid. Examples of organic acids include formic acid, acetic acid, propionic acid, hexanoic acid, glycolic acid, pyruvic acid, lactic acid, malonic acid, succinic acid, malic acid, maleic acid, fumaric acid, trifluoroacetic acid, tartaric acid, citric acid, benzoic acid, cinnamic acid, mandelic acid, methanesulfonic acid, benzenesulfonic acid, stearic acid, and muconic acid.

The term "oxo," as used herein, refers to C=O.

A first aspect of the present invention provides a process for the preparation of ibrutinib of Formula I

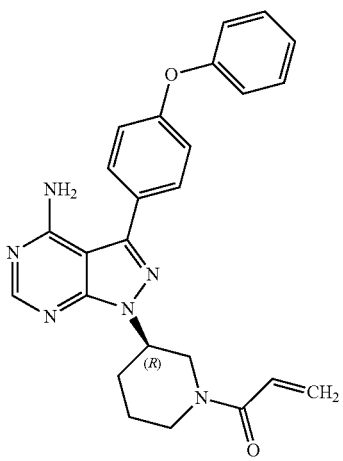

Formula I comprising
a) halogenating a compound of Formula II

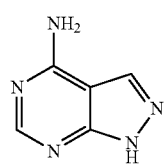

Formula II in the presence of a halogenating agent to obtain a compound of Formula III

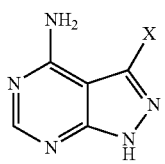

Formula III wherein X is halogen;

b) reacting the compound of Formula III with a compound of Formula IV,

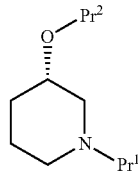

Formula IV wherein Pr¹ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl, and Pr² is a hydroxy-protecting group selected from the group consisting of mesyl, allyl, trityl, benzyl, p-methoxybenzyl, tetrahydropyranyl, and trimethylsilyl, to obtain a compound of Formula V,

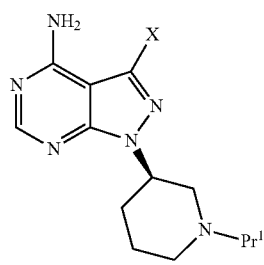

Formula V wherein X is halogen and

Pr¹ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl;

c) deprotecting the compound of Formula V with a deprotecting agent to obtain a compound of Formula VI or its salts,

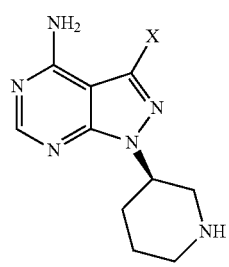

Formula VI wherein X is halogen;

d) reacting the compound of Formula VI or its salts with a compound of Formula VII,

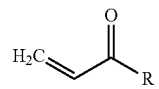

Formula VII wherein R is hydroxy, halogen, tosyl, or mesyl,
to obtain a compound of Formula VIII,

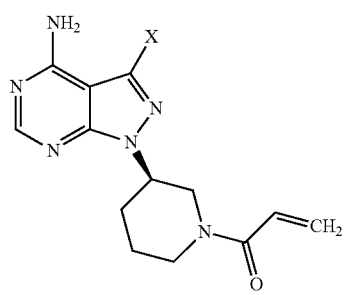

Formula VIII wherein X is halogen; and e) coupling the compound of Formula VIII with a compound of Formula IX, Formula IX wherein R¹ and R² are hydrogen or lower alkyl or R¹ and R² together with the oxygen atoms to which they are attached to form a 5-10 membered heterocyclic ring, which is optionally substituted with lower alkyl, aryl, or oxo, to obtain ibrutinib of Formula I.

A second aspect of the present invention provides a process for the preparation of a compound of Formula VI or its salts,

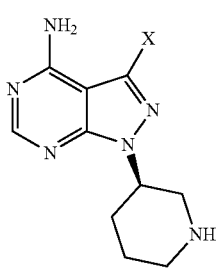

Formula VI wherein X is halogen, comprising
a) reacting a compound of Formula III,

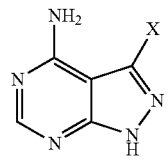

Formula III wherein X is halogen,
with a compound of Formula IV,

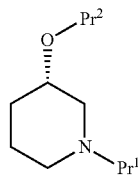

Formula IV wherein Pr¹ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl and Pr² is a hydroxy-protecting group selected from the group consisting of mesyl, allyl, trityl, benzyl, p-methoxybenzyl, tetrahydropyranyl, and trimethylsilyl, to obtain a compound of Formula V,

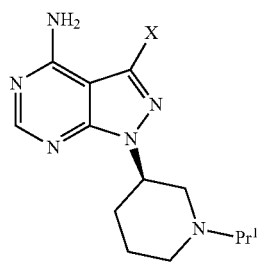

Formula V wherein X is halogen and
Pr¹ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl; and b) deprotecting the compound of Formula V with a deprotecting agent to obtain a compound of Formula VI or its salts.

A third aspect of the present invention provides a process for the preparation of ibrutinib of Formula I

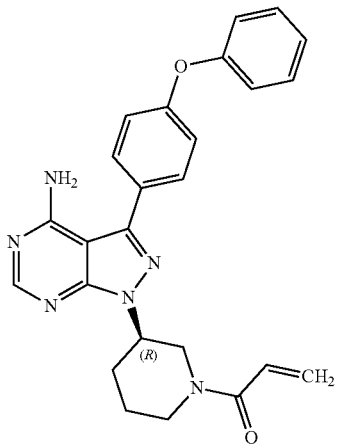

Formula I comprising
a) reacting a compound of Formula III,

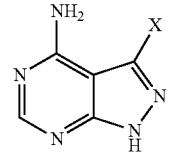

Formula III wherein X is halogen,
with a compound of Formula IV,

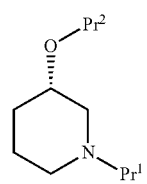

Formula IV wherein Pr¹ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl and Pr² is a hydroxy-protecting group selected from the group consisting of mesyl, allyl, trityl, benzyl, p-methoxybenzyl, tetrahydropyranyl, and trimethylsilyl, to obtain a compound of Formula V,

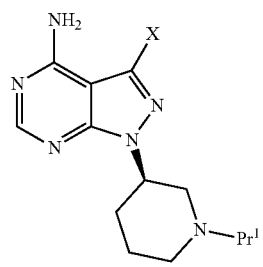

Formula V wherein X is halogen and
Pr¹ is a N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl;

b) deprotecting the compound of Formula V with a deprotecting agent to obtain a compound of Formula VI or its salts,

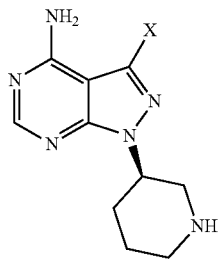

Formula VI wherein X is halogen; and c) converting the compound of Formula VI or its salts to obtain ibrutinib of Formula I.

A fourth aspect of the present invention provides a process for the preparation of a compound of Formula VI or its salts,

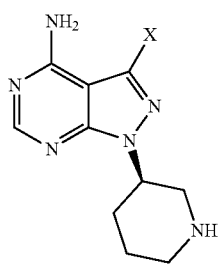

Formula VI wherein X is halogen, comprising deprotecting a compound of Formula V,

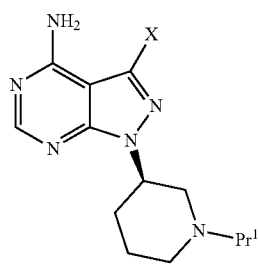

Formula V wherein X is halogen and $Pr^1$ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl, with a deprotecting agent to obtain the compound of Formula VI or its salts.

A fifth aspect of the present invention provides a process for the preparation of ibrutinib of Formula I

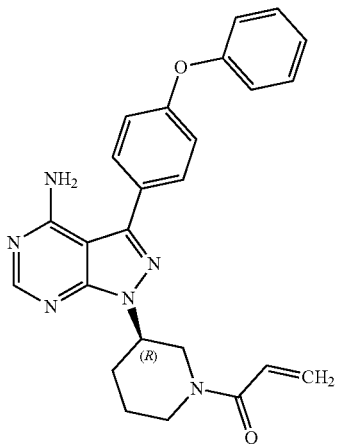

Formula I comprising a) deprotecting a compound of Formula V,

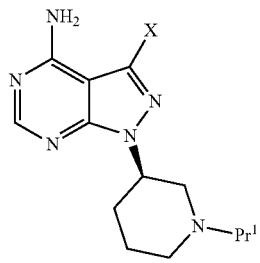

Formula V wherein X is halogen and $Pr^1$ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl, with a deprotecting agent to obtain a compound of Formula VI or its salts,

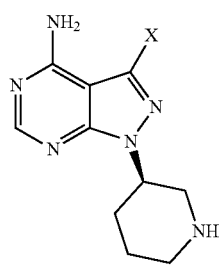

Formula VI wherein X is halogen; and b) converting the compound of Formula VI or its salts to obtain ibrutinib of Formula I.

A sixth aspect of the present invention provides a process for the preparation of a compound of Formula VIII, Formula VIII

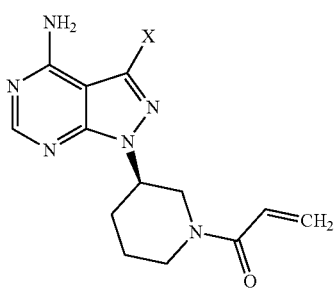

wherein X is halogen,
comprising
a) deprotecting a compound of Formula V,

Formula V

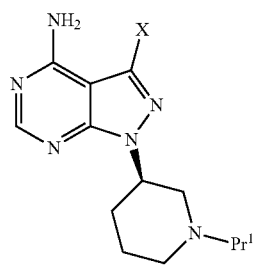

wherein X is halogen and
Pr¹ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl,
with a deprotecting agent to obtain a compound of Formula VI or its salts, Formula VI

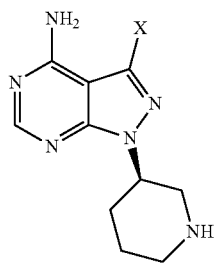

wherein X is halogen; and
b) reacting the compound of Formula VI or its salts with a compound of Formula VII, Formula VII

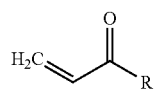

wherein R is hydroxy, halogen, tosyl, or mesyl,
to obtain the compound of Formula VIII.

A seventh aspect of the present invention provides a process for the preparation of ibrutinib of Formula I Formula I

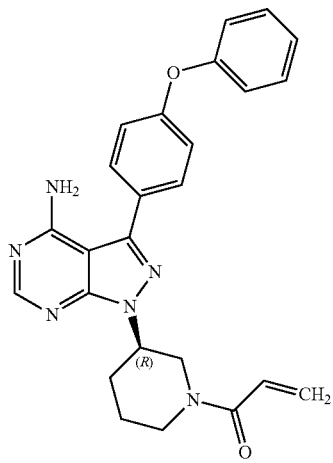

comprising
a) deprotecting a compound of Formula V,

Formula V

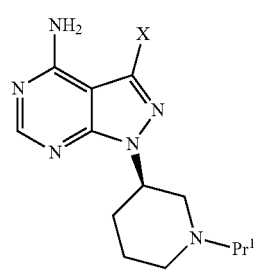

wherein X is halogen and
Pr¹ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl,
with a deprotecting agent to obtain a compound of Formula VI or its salts, Formula VI

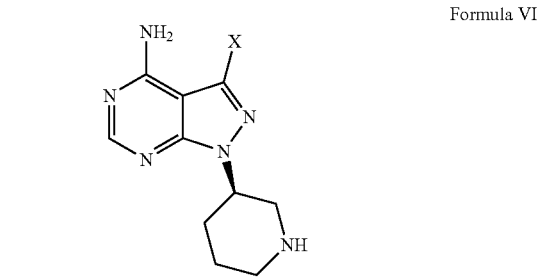

wherein X is halogen;

b) reacting the compound of Formula VI or its salts with a compound of Formula VII,

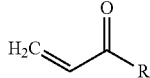

Formula VII wherein R is hydroxy, halogen, tosyl, or mesyl,
to obtain a compound of Formula VIII,

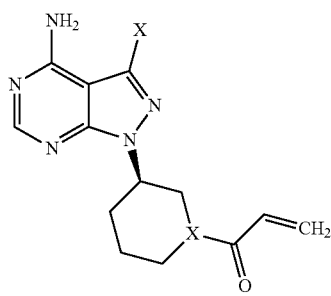

Formula VIII wherein X is halogen; and c) converting the compound of Formula VIII to obtain ibrutinib of Formula I.

An eighth aspect of the present invention provides a process for the preparation of a compound of Formula VIII,

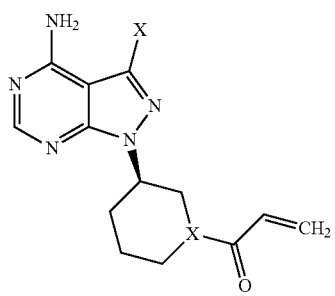

Formula VIII wherein X is halogen,
comprising reacting a compound of Formula VI or its salts,

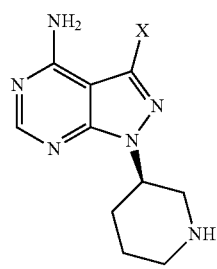

Formula VI wherein X is halogen, with a compound of Formula VII,

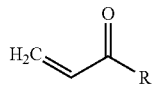

Formula VII wherein R is hydroxy, halogen, tosyl, or mesyl,
to obtain the compound of Formula VIII.

A ninth aspect of the present invention provides a process for the preparation of ibrutinib of Formula I

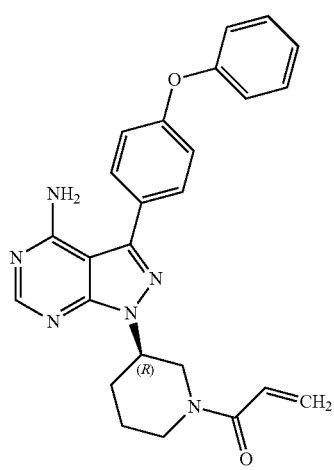

Formula I comprising
a) reacting a compound of Formula VI or its salts,

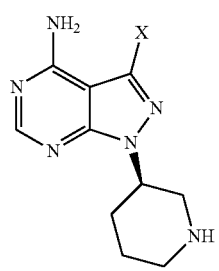

Formula VI wherein X is halogen,
with a compound of Formula VII,

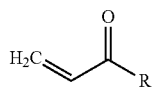

Formula VII wherein R is hydroxy, halogen, tosyl, or mesyl, to obtain the compound of Formula VIII,

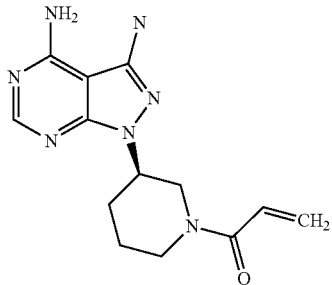

Formula VIII wherein X is halogen; and b) converting the compound of Formula VIII to obtain ibrutinib of Formula I.

A tenth aspect of the present invention provides a process for the preparation of ibrutinib of Formula I

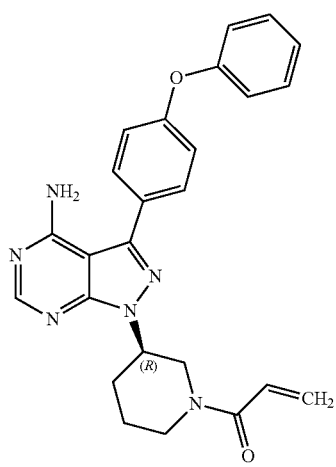

Formula I comprising a) reacting a compound of Formula VI or its salts,

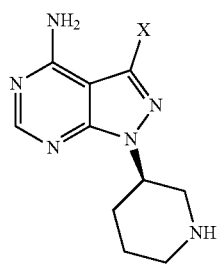

Formula VI wherein X is halogen, with a compound of Formula VII,

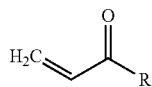

Formula VII wherein R is hydroxy, halogen, tosyl, or mesyl, to obtain a compound of Formula VIII,

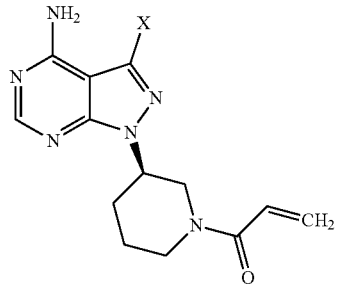

Formula VIII wherein X is halogen; and b) coupling the compound of Formula VIII with a compound of Formula IX,

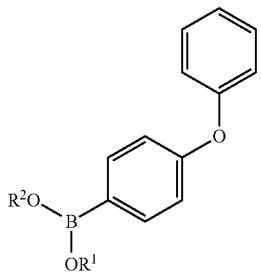

Formula IX wherein $R^1$ and $R^2$ are hydrogen or lower alkyl or $R^1$ and $R^2$ together with the oxygen atoms to which they are attached to form a 5-10 membered heterocyclic ring, which is optionally substituted with lower alkyl, aryl, or oxo, to obtain ibrutinib of Formula I.

An eleventh aspect of the present invention provides a process for the preparation of ibrutinib of Formula I

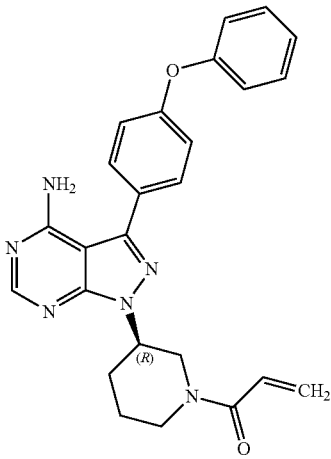

Formula I comprising coupling a compound of Formula VIII,

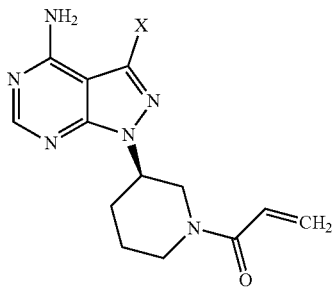

Formula VIII wherein X is halogen,
with a compound of Formula IX,

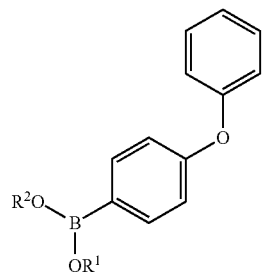

Formula IX wherein $R^1$ and $R^2$ are hydrogen or lower alkyl or $R^1$ and $R^2$ together with the oxygen atoms to which they are attached to form a 5-10 membered heterocyclic ring, which is optionally substituted with lower alkyl, aryl, or oxo, to obtain ibrutinib of Formula I.

The compound of Formula II can be prepared by following the methods provided in the art, such as PCT Publication Nos. WO 2011/094628, WO 2007/126841, WO 2010/006086, and WO 2012/003544; U.S. Publication No. 2007/0293516; U.S. Pat. Nos. 6,921,763 and 8,673,925; Helvetica Chimica Acta, 91(5):958-963 (2008); or by following the method described herein.

The halogenation of the compound of Formula II is carried out in the presence of a halogenating agent in a solvent to obtain the compound of Formula III.

The halogenating agent is selected from the group consisting of N-iodosuccinimide, N-bromosuccinimide, bromine, hydrobromic acid, hydroiodic acid, and N-bromophthalimide.

The solvent is selected from the group consisting of dimethylformamide, dimethylsulfoxide, dichloromethane, and mixtures thereof.

The halogenation of the compound of Formula II is carried out for about 2 hours to about 24 hours, for example, for about 3 hours to about 20 hours.

The halogenation of the compound of Formula II is carried out at a temperature of about 50° C. to about 90° C., for example, of about 55° C. to about 80° C.

The compound of Formula III may optionally be isolated by filtration, decantation, extraction, distillation, evaporation, chromatography, precipitation, concentration, crystallization, centrifugation, or recrystallization. The compound of Formula III may be dried using conventional techniques, for example, drying, drying under vacuum, spray drying, air drying, or agitated thin film drying.

The reaction of the compound of Formula III with the compound of Formula IV is carried out in the presence of a base and a catalyst in a solvent to obtain the compound of Formula V.

The compound of Formula IV (when $Pr^1$ is N-tert-butoxycarbonyl (Boc) and $Pr^2$ is methylsulfonyl) is prepared by sulfonylation of tert-butyl (3S)-3-hydroxypyridine-1-carboxylate using a sulfonyl halide selected from the group consisting of methanesulfonyl chloride, benzenesulfonyl chloride, and p-toluenesulfonyl chloride, in the presence of a base selected from the group consisting oftriethylamine, isopropylamine, pyridine, N,N-diisopropylethylamine, dimethylaminopyridine, and N-methylmorpholine, in a solvent selected from the group consisting of toluene, dioxane, benzene, hexane, chloroform, diethyl ether, and mixtures thereof.

The base is selected from the group consisting of cesium carbonate, potassium carbonate, sodium carbonate, potassium phosphate, sodium hydroxide, N,N-diisopropylethylamine, tert-butylamine, potassium hydroxide, potassium tert-butoxide, and sodium-tert-butoxide.

The catalyst is selected from the group consisting of dimethylaminopyridine, benzyltrimethylammonium chloride, hexadecyltributylphosphonium bromide, tetra-n-butylammonium bromide, and methyltrioctylammonium chloride.

The solvent is selected from the group consisting of N-methylpyrrolidone, dimethylformamide, dimethylacetamide, dimethylsulfoxide, tetrahydrofuran, and mixtures thereof.

The reaction of the compound of Formula III with the compound of Formula IV is carried out for about 4 hours to about 30 hours, for example, for about 5 hours to about 24 hours.

The reaction of the compound of Formula III with the compound of Formula IV is carried out at a temperature of about 50° C. to about 150° C., for example, of about 60° C. to about 120° C.

The compound of Formula V may optionally be isolated by filtration, decantation, extraction, distillation, evaporation, chromatography, precipitation, concentration, crystallization, centrifugation, or recrystallization. The compound of Formula V may be dried using conventional techniques, for example, drying, drying under vacuum, spray drying, air drying, or agitated thin film drying.

The deprotection of the compound of Formula V is carried out with a deprotecting agent in a solvent, optionally in the presence of a base, to obtain the compound of Formula VI.

Alternatively, the deprotection of the compound of Formula V is carried out with a deprotecting agent in a solvent to obtain a salt of the compound of Formula VI, which on reaction with a base provides the compound of Formula VI.

The deprotecting agent is selected from the group consisting of hydrochloric acid, alcoholic hydrochloric acid, ethereal hydrochloric acid, trifluoroacetic acid, hydrobromic acid, and sulfuric acid.

The solvent is selected from the group consisting of methanol, ethanol, n-propanol, isopropanol, tert-butanol, dichloromethane, chloroform, carbon tetrachloride, and mixtures thereof.

When alcoholic hydrochloric acid or ethereal hydrochloric acid are used as deprotecting agents, these serve as a solvent also.

Examples of alcoholic solvents for the preparation of alcoholic hydrochloric acid include methanol, ethanol, n-propanol, isopropanol, tert-butanol, and mixtures thereof.

Examples of ethereal solvents for the preparation of ethereal hydrochloric acid include dioxane, methyl tert-butyl ether, and mixtures thereof.

The base is selected from the group consisting of triethylamine, dimethylaminopyridine, isopropylamine, diisopropylethylamine, pyridine, and tributylamine.

The deprotection of the compound of Formula V is carried out for about 10 minutes to about 3 hours, for example, for about 20 minutes to about 2 hours.

The deprotection of the compound of Formula V is carried out at a temperature of about 20° C. to about 80° C., for example, of about 40° C. to about 60° C.

The compound of Formula VI or its salts may optionally be isolated by filtration, decantation, extraction, distillation, evaporation, chromatography, precipitation, concentration, crystallization, centrifugation, or recrystallization. The compound of Formula VI or its salts may be dried using conventional techniques, for example, drying, drying under vacuum, spray drying, air drying, or agitated thin film drying.

The reaction of the compound of Formula VI or its salts with the compound of Formula VII is carried out in the presence of a base in a solvent to obtain the compound of Formula VIII.

The compound of Formula VII is prepared by the halogenation of acrylic acid with a halogenating agent selected from the group consisting of oxalyl chloride, phosgene, and thionyl chloride, optionally in-situ, in a solvent selected from the group consisting of dichloromethane, dimethylformamide, dimethylsulfoxide, chloroform, dichloroethane, carbon tetrachloride, and mixtures thereof.

The base is selected from the group consisting of triethylamine, isopropylamine, pyridine, N,N-diisopropylethylamine, dimethylaminopyridine, and N-methylmorpholine.

The solvent is selected from the group consisting of dichloromethane, chloroform, dichloroethane, carbon tetrachloride, and mixtures thereof.

Alternatively, the reaction of the compound of Formula VI or its salts with the compound of Formula VII is carried out in the presence of a coupling agent in a solvent to obtain the compound of Formula VIII.

The coupling agent is selected from the group consisting of N,N'-dicyclohexylcarbodiimide, 1-ethyl-3-(3-dimethylaminopropyl)carbodiimide, N-[(dimethylamino)-1H-1,2,3-triazolo[4,5-b]pyridylmethylene]-N-methylmethanaminium hexafluorophosphate N-oxide, and benzotriazol-1-yl-N-oxy-tris(pyrrolidino)phosphonium hexafluorophosphate.

The solvent is selected from the group consisting of dichloromethane, chloroform, dichloroethane, carbon tetrachloride, and mixtures thereof.

The reaction of the compound of Formula VI or its salts with the compound of Formula VII is carried out for about 10 minutes to about 6 hours, for example, for about 20 minutes to about 4 hours.

The reaction of the compound of Formula VI or its salts with the compound of Formula VII is carried out at a temperature of about 15° C. to about 40° C., for example, of about 20° C. to about 30° C.

The compound of Formula VIII may optionally be isolated by filtration, decantation, extraction, distillation, evaporation, chromatography, precipitation, concentration, crystallization, centrifugation, or recrystallization. The compound of Formula VIII may be dried using conventional techniques, for example, drying, drying under vacuum, spray drying, air drying, or agitated thin film drying.

The coupling of the compound of Formula VIII with the compound of Formula IX is carried out in the presence of a base and a catalyst in a solvent to obtain ibrutinib of Formula I.

The compound of Formula IX used for the preparation of ibrutinib of Formula I is commercially available.

The base is selected from the group consisting of cesium carbonate, potassium carbonate, sodium carbonate, potassium phosphate, sodium hydroxide, N,N-diisopropylethylamine, tert-butylamine, potassium hydroxide, potassium tert-butoxide, and sodium-tert-butoxide.

The catalyst is selected from the group consisting of a [1,1'-bis(diphenylphosphino)ferrocene]-dichloropalladium (II) complex with dichloromethane, bis(triphenylphosphine) palladium(II) dichloride, dichlorobistriphenylphosphine palladium (II), tetrakistriphenylphosphine palladium (0), and palladium(II) acetate.

The solvent is selected from the group consisting of dioxane, water, n-propanol, isopropanol, methanol, ethanol, acetone, toluene, acetonitrile, dimethylformamide, tetrahydrofuran, and mixtures thereof.

The coupling of the compound of Formula VIII with a compound of Formula IX is carried out for about 2 hours to about 20 hours, for example, for about 3 hours to about 16 hours.

The coupling of the compound of Formula VIII with a compound of Formula IX is carried out at a temperature of about 50° C. to about 120° C., for example, of about 75° C. to about 110° C.

Ibrutinib of Formula I may optionally be isolated by filtration, decantation, extraction, distillation, evaporation, chromatography, precipitation, concentration, crystallization, centrifugation, or recrystallization. Ibrutinib of Formula I may be dried using conventional techniques, for example, drying, drying under vacuum, spray drying, air drying, or agitated thin film drying.

A twelfth aspect of the present invention provides a compound of Formula VIa or its salts.

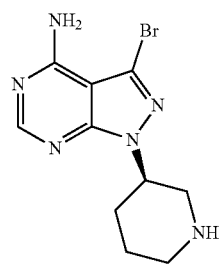

Formula VIa

A thirteenth aspect of the present invention provides a salt of a compound of Formula VIb.

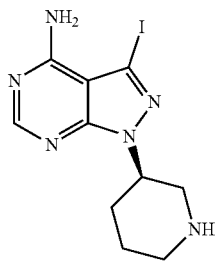

Formula VIb

A fourteenth aspect of the present invention provides a compound of Formula VIII,

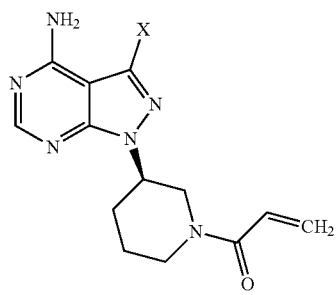

Formula VIII wherein X is halogen.

A fifteenth aspect of the present invention provides the use of a compound of Formula VI or its salt for the preparation of ibrutinib,

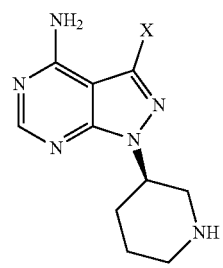

Formula VI wherein X is halogen.

A sixteenth aspect of present invention provides the use of a compound of Formula VIII for the preparation of ibrutinib,

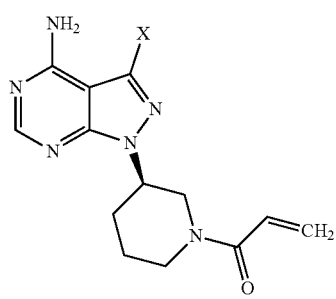

Formula VIII wherein X is halogen.

Methods

NMR spectrum was recorded using a Bruker® AVANCE III (400 MHz) NMR spectrometer.

Mass spectrum was recorded on a MASS (API 2000) LC/MS/MS system, QTRAP® LC/MS/MS system.

The following examples are set forth to demonstrate general synthetic procedures for the preparation of representative compounds. The examples are provided to illustrate particular aspects of the disclosure and do not limit the scope of the present invention.

EXAMPLES

Example 1

Preparation of 1H-pyrazolo[3,4-d]pyrimidin-4-amine (Formula II)

5-Amino-1H-pyrazole-4-carbonitrile (20 g) was added to formamide (130 mL), and the reaction mixture was heated under nitrogen at 130° C. for 24 hours. Water (200 mL) was added to the reaction mixture, and the mixture was stirred at 0° C. to 5° C. for 2 hours. The solid obtained was filtered followed by washing with water (30×2 mL), and was kept in an oven at 50° C. for 16 hours to obtain the title compound.

Yield: 19.7 g

Example 2

Preparation of 3-iodo-1H-pyrazolo[3,4-d]pyrimidin-4-amine (Formula III, when X is iodo)

A mixture of 1H-pyrazolo[3,4-d]pyrimidin-4-amine (Formula II, 20 g), N-iodosuccinimide (41.6 g) and dimethylformamide (300 mL) was stirred at 75° C. to 80° C. for 16 hours. Water (1 L) was added to the reaction mixture, and then the mixture was stirred at 15° C. for 4 hours. The solid obtained was filtered, then washed with water (100 mL), and then washed with cold ethanol (60 mL). The resulting solid was dried at 45° C. under vacuum for 16 hours to obtain the title compound.

Yield: 26.8 g

Example 3

Preparation of 3-bromo-1H-pyrazolo[3,4-d]pyrimidin-4-amine (Formula III, when X is bromo)

A mixture of 1H-pyrazolo[3,4-d]pyrimidin-4-amine (Formula II, 25 g), N-bromosuccinimide (36.2 g), and dimethylformamide (150 mL) was stirred at 60° C. for 4 hours. The reaction mixture was gradually cooled to 25° C. to 30° C., and then filtered. Deionized water (750 mL) was added to the filtrate, and the mixture was stirred at 25° C. to 30° C. for 30 minutes. The solid obtained was filtered, then washed with deionized water (50 mL), and then dried under vacuum at 60° C. for 10 hours to 12 hours to obtain the title compound.

Yield: 27.9 g

Example 4

Preparation of tert-butyl (3S)-3-[(methylsulfonyl)oxy]piperidine-1-carboxylate (Formula IV, when Pr$^1$ is N-tert-butoxycarbonyl (Boc) and Pr$^2$ is methylsulfonyl)

tert-Butyl (3S)-3-hydroxypiperidine-1-carboxylate (25 g) and triethylamine (30 g) were added to toluene (250 mL) at 25° C. to obtain a reaction mixture. The reaction mixture was cooled to 0° C. to 5° C. A solution of mesyl chloride (22.5 g) in toluene (100 mL) was added drop-wise to the solution over a period of one hour at 0° C. to 5° C. The reaction mixture was stirred for 2 hours at room temperature. Water (250 mL) was added to the reaction mixture, and the mixture was stirred to separate the organic layer. The organic layer was washed with water (100 mL), and then evaporated under vacuum to obtain a pale yellow viscous crude material (52 g). Toluene (30 mL) was added at 45° C., and a solid was obtained by the slow addition of hexane (150 mL) over 15 minutes. The mixture was stirred for one hour at room temperature. The solid was filtered, and then kept in a vacuum oven at 45° C. for 3 hours to obtain the title compound.

Yield: 31 g

Example 5

Preparation of tert-butyl (3R)-3-(4-amino-3-iodo-1H-pyrazolo[3,4-d]pyrimidin-1-yl)piperidine-1-carboxylate (Formula V, when X is iodo and $Pr^1$ is Boc)

A mixture of 3-iodo-1H-pyrazolo[3,4-d]pyrimidin-4-amine (Formula III, when X is iodo, 18 g), cesium carbonate (51.8 g), and dimethylaminopyridine (0.88 g) was added to N-methylpyrrolidinone (400 mL) under nitrogen at room temperature. The temperature of the reaction mixture was raised to 70° C. A solution of tert-butyl (3S)-3-[(methylsulfonyl)oxy]piperidine-1-carboxylate (Formula IV, when $Pr^1$ is Boc and $Pr^2$ is methylsulfonyl, 29 g) in N-methylpyrrolidone (150 mL) was added drop-wise to the solution over a period of one hour at 70° C. The reaction mixture was stirred overnight at 70° C. Water (1.7 L) was added to the reaction mixture, then the mixture was stirred at 5° C. for 3 hours, and then stirred overnight at room temperature. The yellowish solid product was filtered, then washed with water (100 mL). The resulting solid was dried at 45° C. under vacuum for 9 hours to obtain the title compound.

Yield: 13.8 g

Example 6

Preparation of tert-butyl (3R)-3-(4-amino-3-bromo-1H-pyrazolo[3,4-d]pyrimidin-1-yl)piperidine-1-carboxylate (Formula V, when X is bromo, and $Pr^1$ is Boc)

A mixture of 3-bromo-1H-pyrazolo[3,4-d]pyrimidin-4-amine (Formula III, when X is bromo, 10 g), potassium carbonate (12.9 g), and tert-butyl (3S)-3-[(methylsulfonyl)oxy]piperidine-1-carboxylate (Formula IV, when $Pr^1$ is Boc and $Pr^2$ is methylsulfonyl, 14.35 g) was added to dimethylformamide (100 mL) at 25° C. to 30° C. The reaction mixture was stirred at 120° C. for 5 hours to 6 hours. The remaining tert-butyl (3S)-3-[(methylsulfonyl)oxy]piperidine-1-carboxylate (Formula IV, when $Pr^1$ is Boc and $Pr^2$ is methylsulfonyl, 6.5 g) was added to the mixture, and then the reaction mixture was stirred overnight at 120° C., and then cooled to 25° C. to 30° C. Water (1.25 L) was added to the mixture, and the product was extracted with ethyl acetate (2×500 mL) at 25° C. to 30° C. Excess ethyl acetate was recovered under vacuum at a temperature not exceeding 50° C. Hexane (250 mL) was added to the mixture, and the reaction mixture was stirred overnight at 25° C. to 30° C. A sticky mass was obtained and used as such for the next reaction.

Example 7

Preparation of 3-iodo-1-[(3R)-piperidin-3-yl]-1H-pyrazolo[3,4-d]pyrimidin-4-amine monohydrochloride (hydrochloride salt of Formula VI, when X is iodo)

A mixture of tert-butyl (3R)-3-(4-amino-3-iodo-1H-pyrazolo[3,4-d]pyrimidin-1-yl)piperidine-1-carboxylate (Formula V, when X is iodo and $Pr^1$ is Boc, 1.7 g) and methanolic hydrochloric acid (15 mL) was stirred for 30 minutes at 45° C. The reaction mixture was evaporated to complete dryness at a temperature not more than 45° C., then washed with ethyl acetate (30 mL), and then re-evaporated to complete dryness at a temperature not exceeding 45° C. to obtain the title compound.

Yield: 1.2 g
$^1$H NMR (DMSO-$d_6$, 400 MHz) δ 1.8-2.0 (m, 2H), 2.0-2.2 (m, 2H), 3.2-3.5 (m, 3H), 2.99-3.0 (m, 1H), 5.12 (s, 1H), 8.66 (s, 1H), 9.52-9.72 (bs, 2H)
Mass m/z=345.3 [M+H]$^+$ Example 8

Preparation of 3-bromo-1-[(3R)-piperidin-3-yl]-1H-pyrazolo[3,4-d]pyrimidin-4-amine (Formula VI, when X is bromo)

tert-Butyl (3R)-3-(4-amino-3-bromo-1H-pyrazolo[3,4-d]pyrimidin-1-yl)piperidine-1-carboxylate (Formula V, when X is bromo and $Pr^1$ is Boc, 10 g) was added to methanolic hydrochloric acid (100 mL) at 25° C. to 30° C. The reaction mixture was heated at 45° C., and then stirred for 2 hours, then evaporated to complete dryness at a temperature not exceeding 50° C. Ethyl acetate (100 mL) was added to the crude material, and then the reaction mass was re-evaporated to dryness to obtain a sticky mass. Deionized water (100 mL) and triethylamine (10 mL) were added to the mixture, and then the product was extracted with dichloromethane (2×100 mL) at 25° C. to 30° C. The excess dichloromethane was recovered completely under vacuum at a temperature not exceeding 40° C. The material obtained was dried under vacuum at room temperature for 8 hours to 10 hours to obtain the title compound.

Yield: 3.2 g
$^1$H NMR (CDCl$_3$, 400 MHz) δ 1.62-1.68 (m, 1H), 1.85-1.90 (m, 1H), 2.09-2.31 (m, 2H), 2.71-2.75 (m, 1H), 3.14-3.19 (m, 1H), 3.23-3.27 (m, 2H), 4.72-4.77 (m, 1H), 8.31 (s, 1H)
Mass m/z=299.2 [M+2]

Example 9

Preparation of 1-[(3R)-3-(4-amino-3-iodo-1H-pyrazolo[3,4-d]pyrimidin-1-yl)piperidin-1-yl]prop-2-en-1-one (Formula VIII, when X is iodo)

Oxalyl chloride (0.28 g) was added to a solution of acrylic acid (0.1 g) and dimethylformamide (0.050 mL) in dichloromethane (5 mL) at room temperature. The reaction mixture was stirred for 90 minutes at room temperature to obtain a pale yellow clear 2-propenoyl chloride solution (Formula VII, when R is chloro). 3-Iodo-1-[(3R)-piperidin-3-yl]-1H- pyrazolo[3,4-d]pyrimidin-4-amine monohydrochloride (hydrochloride salt of Formula VI, 0.5 g) was suspended in dichloromethane (5 mL) to obtain a reaction mixture. Triethylamine (0.32 g) was added to the reaction mixture under nitrogen at room temperature. The clear solution was maintained at 0° C. to 5° C. The 2-propenoyl chloride solution as prepared above was added drop-wise to the mixture over a period of 30 minutes. The reaction mixture was stirred at 20° C. to 25° C. for 3 hours. Water (25 mL) and dichloromethane (20 mL) were added to the reaction mixture, and the separated organic layer was evaporated to dryness. The solid obtained was purified by column chromatography using a gradient elusion with ethyl acetate to 5% methanol-ethyl acetate to obtain a pale yellow solid, which was dried under vacuum at a temperature not exceeding 40° C. to obtain the title compound.

Yield: 0.25 g $^1$H NMR (DMSO-$d_6$, 400 MHz) δ 1.6 (bs, 1H), 1.8-1.9 (bs, 1H), 2.0-2.3 (m, 2H), 3.0-3.2 (m, 1H), 3.5-3.8 (m, 1H), 4.2-4.4 (m, 1H), 4.4-4.7 (m, 2H), 5.6-5.8 (dd, 1H), 6.05-6.2 (m, 1H), 6.6-6.9 (m, 1H), 8.21 (s, 1H)

Mass m/z=399.1 [M+H]$^+$

Example 10

Preparation of 1-[(3R)-3-(4-amino-3-bromo-1H-pyrazolo[3,4-d]pyrimidin-1-yl)piperidin-1-yl]prop-2-en-1-one (Formula VIII, when X is bromo)

3-Bromo-1-[(3R)-piperidin-3-yl]-1H-pyrazolo[3,4-d]pyrimidin-4-amine (Formula VI when X is bromo, 3.0 g) in dichloromethane (50 mL) was added to triethylamine (3.1 g) under nitrogen at room temperature. The clear solution was maintained at 0° C. to 5° C., and a 2-propenoyl chloride solution (Formula VII, when R is chloro, 0.9 mL) in dichloromethane (50 mL) was added drop-wise to the mixture over a period of 30 minutes. The reaction mixture was stirred at 20° C. to 25° C. for 2 hours. Deionized water (50 mL) was added, and then the reaction mixture was stirred for 10 minutes to 15 minutes at 25° C. to 30° C. The separated organic layer was washed with deionized water (50 mL). The organic layer was separated, and then evaporated to dryness under vacuum at a temperature not exceeding 35° C. to obtain the title compound.

Yield: 2.7 g $^1$H NMR (CDCl$_3$, 400 MHz) δ 1.8-1.71 (m, 1H), 1.95-1.99 (m, 2H), 2.21-2.28 (m, 2H), 2.73-2.95 (m, 2H), 3.12-3.30 (m, 1H), 4.76-4.78 (m, 1H), 6.13-6.40 (m, 2H), 6.57-6.59 (m, 1H), 8.31 (s, 1H)

Mass m/z=353.2 [M+2]

Example 11

Preparation of Ibrutinib (Formula I)

1-[(3R)-3-(4-Amino-3-iodo-1H-pyrazolo[3,4-d]pyrimidin-1-yl)piperidin-1-yl]prop-2-en-1-one (Formula VIII, when X is iodo, 0.35 g), cesium carbonate (0.7 g), and (4-phenoxyphenyl)boronic acid (Formula IX, when R$^1$ and R$^2$ are hydrogen, 0.38 g) were added to a mixture of dioxane (20 mL) and water (5 mL) under nitrogen. [1,1'-Bis(diphenylphosphino)ferrocene]-dichloropalladium(II) complex with dichloromethane (0.1 g) was added, and then the reaction mixture was stirred at 80° C. for 16 hours. The reaction mixture was diluted with water (5 mL) and ethyl acetate (25 mL). The organic layer was separated, and the solvent was evaporated to obtain a dark viscous crude material. The crude material obtained was purified by column chromatography using a gradient elusion with dichloromethane to 5% methanol-dichloromethane to obtain the title compound.

Yield: 0.24 g

Example 12

Preparation of Ibrutinib (Formula I)

1-[(3R)-3-(4-Amino-3-bromo-1H-pyrazolo[3,4-d]pyrimidin-1-yl)piperidin-1-yl]prop-2-en-1-one (Formula VIII, when X is bromo, 2.50 g), potassium carbonate (4.92 g), and (4-phenoxyphenyl)boronic acid (Formula IX, when R$^1$ and R$^2$ are hydrogen, 2.28 g) were dissolved in a mixture of dioxane (40 mL) and water (25 mL) under nitrogen. Bis(triphenylphosphine)palladium(II) dichloride (0.25 g) was added to the mixture, and the reaction mixture was stirred at 100° C. to 105° C. for 4 hours. The reaction mixture was diluted with water (20 mL) and ethyl acetate (50 mL). The organic layer was separated, and the solvent was evaporated to obtain a dark viscous crude material. Methyl tert-butyl ether (50 mL) was added to the mixture, and then the reaction mixture was stirred for one hour at 25° C. to 30° C. The material was filtered, and then washed with methyl tert-butyl ether (10 mL) at 25° C. to 30° C. The material obtained was dried under vacuum for 4 hours to 5 hours at 25° C. to 30° C. to obtain the title compound.

Yield: 1.25 g.

We claim:

1. A process for the preparation of a compound of Formula VIII,

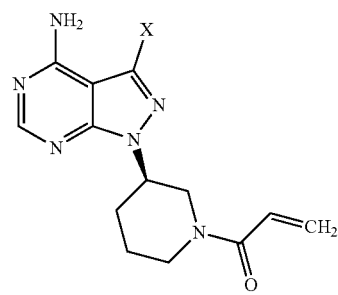

Formula VIII wherein X is halogen,
comprising reacting a compound of Formula VI or its salts,

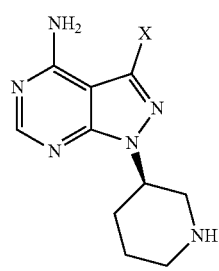

Formula VI wherein X is halogen;

with a compound of Formula VII,

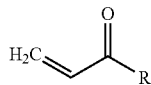
Formula VII wherein R is hydroxy, halogen, tosyl, or mesyl, to obtain the compound of Formula VIII.

2. The process according to the claim 1, wherein the reaction of the compound of Formula VI or its salts with the compound of Formula VII is carried out in the presence of a base in a solvent.

3. The process according to the claim 1, wherein the reaction of the compound of Formula VI or its salts with the compound of Formula VII is carried out in the presence of a coupling agent in a solvent.

4. The process according to the claim 1, wherein the compound of Formula VI or its salts is prepared by deprotecting a compound of Formula V

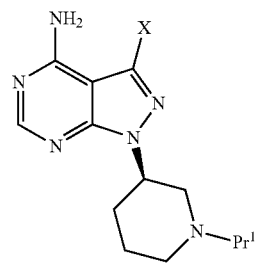
Formula V wherein X is halogen and

Pr$^1$ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl, with a deprotecting agent.

5. The process according to the claim 4, wherein the deprotection of the compound of Formula V is carried out with a deprotecting agent in a solvent, optionally in the presence of a base.

6. The process according to the claim 4, wherein the deprotection of the compound of Formula V is carried out with a deprotecting agent to obtain a salt of the compound of Formula VI in a solvent, which is further treated with a base.

7. The process according to the claim 4, wherein the compound of Formula V is prepared by reacting a compound of Formula III,

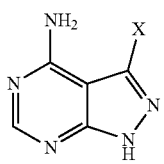
Formula III wherein X is halogen, with a compound of Formula IV,

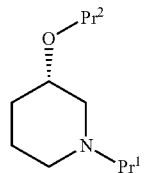
Formula IV wherein Pr$^1$ is an N-protecting group selected from the group consisting of tert-butyloxycarbonyl, benzyloxycarbonyl, 2-(trimethylsilyl)ethoxycarbonyl, benzyl, benzoyl, carbamate, tosyl, and p-methoxybenzyl carbonyl and Pr$^2$ is a hydroxy-protecting group selected from the group consisting of mesyl, allyl, trityl, benzyl, p-methoxybenzyl, tetrahydropyranyl, and trimethylsilyl.

8. The process according to the claim 7, wherein the compound of Formula III is reacted with the compound of Formula IV in the presence of a base and a catalyst in a solvent.

9. The process according to the claim 7, wherein the compound of Formula III is prepared by halogenating a compound of Formula II

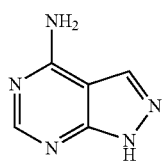
Formula II in the presence of a halogenating agent in a solvent.

10. The process according to the claim 1, wherein the compound of the Formula VIII is further converted to ibrutinib of Formula I

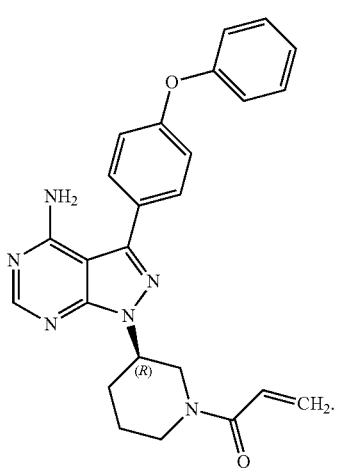
Formula I

11. The process according to the claim 1, wherein the compound of the Formula VIII is further converted to ibrutinib of Formula I Formula I

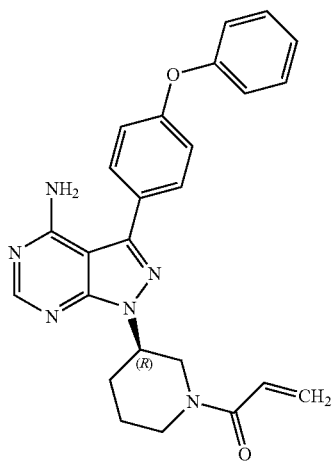

comprising coupling the compound of the Formula VIII,

Formula VIII

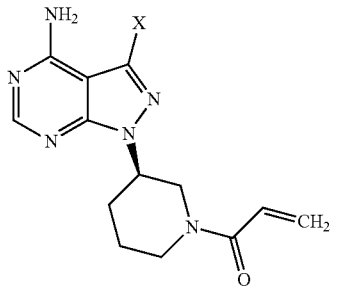

with a compound of Formula IX,

Formula IX

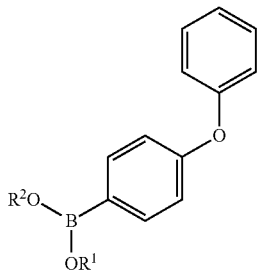

wherein $R^1$ and $R^2$ are hydrogen or lower alkyl or $R^1$ and $R^2$ together with the oxygen atoms to which they are attached to form a 5-10 membered heterocyclic ring, which is optionally substituted with lower alkyl, aryl, or oxo, to obtain the ibrutinib of Formula I.

12. The process according to the claim 11, wherein the coupling the compound of the Formula VIII with the compound of Formula IX is carried out in the presence of a base and a catalyst in a solvent.

* * * * *